United States Patent
Gaven et al.

(10) Patent No.: US 7,611,848 B2
(45) Date of Patent: Nov. 3, 2009

(54) METHOD FOR SELECTING ALLOSTERIC REGULATORS OF CLASS III G PROTEIN-COUPLED RECEPTORS

(75) Inventors: Florence Gaven, Saint-Mathieu-de-Trevier (FR); Cyril Goudet, Montpellier (FR); Jean-Philippe Pin, Montpellier (FR); Laurent Prezeau, Castelnau le Lez (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 10/557,986

(22) PCT Filed: May 11, 2004

(86) PCT No.: PCT/FR2004/001140

§ 371 (c)(1),
(2), (4) Date: Dec. 29, 2006

(87) PCT Pub. No.: WO2004/106932

PCT Pub. Date: Dec. 9, 2004

(65) Prior Publication Data

US 2008/0058430 A1    Mar. 6, 2008

(30) Foreign Application Priority Data

May 22, 2003  (FR)  ................................. 03 06136

(51) Int. Cl.
    *G01N 33/567*  (2006.01)
    *C07K 14/705*  (2006.01)
(52) U.S. Cl. ......................... 435/7.2; 435/7.1; 435/7.21; 436/501
(58) Field of Classification Search ....................... None
    See application file for complete search history.

(56) References Cited

OTHER PUBLICATIONS

Parmentier et al. a Model for the Functioning of Family 3 GPCRs, Jun. 2002, Trends in Pharmacological Sciences 23(6):268-274.*
Fabrice Ango et al., "A simple method to transfer plasmid DNA into neuronal primary cultures: functional expression of the mGlu$_5$ receptor in cerebellar granule cells", Neuropharmacology, 1999, pp. 793-803, No. 38.
Joel Bockaert et al., "Molecular tinkering of G protein-coupled receptors: an evolutionary success", The EMBO Journal, 1999, pp. 1723-1729, vol. 18, No. 7.
Edward M. Brown et al., "Extracelluar Calcium Sensing and Extracellular Calcium Signaling", Physiological Reviews, Jan. 20001, pp. 239-297, vol. 81, No. 1.
P. Jeffrey Conn et al., Pharmacology and Functions of Metabotropic Glutamate Receptors, Annu. Rev. Pharmacol. Toxicol., 1997, pp. 205-237, vol. 37.
Beatrice Duthey et al., "A Single Subunit (GB2) Is Required for G-protein Activation by the Heterodimeric GABA$_B$ Receptor", The Journal of Biological Chemistry, 2002, pp. 3236-3241, vol. 277, No. 5.
Miloslav Franek et al., "The heteromeric GABA-B receptor recognizes G-protein α subunit C-termini", Neuropharmacology, 1999, pp. 1657-1666, vol. 38.
Jesus Gomeza et al., "Coupling of Metabotropic Glutamate Receptors 2 and 4 to $G_{a15}$ $G_{a16}$, and Chimeric $G_{aq/i}$ Proteins: Characterization of New Antagonists", Molecular Pharmacology, 1996, pp. 923-930, vol. 50.
Lance G. Hammerland et al., "Domains Determining Ligand Specificity for $Ca^{2+}$Receptors", Molecular Pharmacology, 1999, pp. 642-648, vol. 55.
Lance G. Hammerland et al., "Allosteric Activation of the $Ca^{2+}$Receptor Expressed in Xenopus laevis Oocytes by NPS 467 or NPS 568", Molecular Pharmacology, 1998, pp. 1083-1088, vol. 53.
Klemens Kaupmann et al., "GABA$_B$-receptor subtypes assemble into functional heteromeric complexes", Nature, Dec. 17, 1998, pp. 683-687, vol. 396.
A.E. Kingston et al., "LY341495 is a nanomolar potent and selective antagonist of group II metabotropic glutamate receptors", Neuropharmacology, 1998, pp. 1-12, vol. 37.
A.E. Kingston et al., "Sulphur-containing amino acids are agonists for group 1 metabotropic receptors expressed in clonal RGT cell lines", Neuropharmacology, 1998, pp. 277-287, vol. 37.
Julie Kniazeff et al., "No Ligand Binding in the GB2 Subunit of the GABA$_B$ Receptor Is Required for Activation and Allosteric Interaction between the subunits", The Journal of Neuroscience, Sep. 1, 2002, pp. 7352-7361, vol. 22, No. 17.
Graeme Milligan, "Principles: Extending the utility of [$^{35}$S]GTYPγS biding assays", Trends in Pharmacological Sciences, Feb. 2003, pp. 87-90, vol. 24, No. 2.

(Continued)

*Primary Examiner*—John D Ulm
(74) *Attorney, Agent, or Firm*—Arent Fox LLP

(57) ABSTRACT

A method for identifying and selecting a compound acting as an allosteric regulator of a GPCR-III is described. A method comparing the activity level of a recombinant GPCR-III (GPCR-III-Δ), essentially depleted of the extracellular domain of the corresponding native GPCR-III, in the presence of a given compound, with the activity level of the same GPCR-III-Δ is described. A method of identifying positive or negative allosteric regulators of GPCRs-III is described.

13 Claims, 7 Drawing Sheets

OTHER PUBLICATIONS

Greg Nelson et al., "An amino-acid taste receptor", Nature, Mar. 14, 2002, pp. 1999-202, vol. 416.

Edward F. Nemeth et al., "Calcimimetics with potent and selective activity on the parathyroid calcium receptor", Proc. Natl. Acad. Sci. USA, Mar. 1998, pp. 4040-4045, vol. 95.

Adriana Pagano et al., "The Non-competitive Antagonists 2-Methyl-6-(phenylethynyl)pyridine and 7-Hydroxyiminocyclopropan [b]chromen-1a-carboxylic Acid Ethyl Ester Interact with Overlapping Binding Pcokets nit he Transmembrane Region of Group I Metabotropic Glutamate Receptors", The Journal of Biological Chemistry, 2000, pp. 33750-33758, vol. 275, No. 43.

Adriana Pagano et al., "C-Terminal Interaction is Essential for Surface Trafficking But Not for Heteromeric Assemby of $GABA_B$ Receptors", The Journal of Neuroscience, Feb. 15, 2001, pp. 1189-1202, vol. 21, No. 4.

Marie-Laure Parmentier et al., "Cloning and Functional Expression of a Drosophila Metabotropic Glutamate Receptor Expressed in the Embryonic CNS", The Journal of Neuroscience, Nov. 1, 1996, pp. 6687-6694, vol. 16, No. 21.

Jean-Philippe Pin et al., Evolution, structure, and activation mechanism of family 3/C G-protein-coupled receptors, Pharmacology & Therapeutics 98, 2003, pp. 325-354.

Kausik Ray et al., "Calindol, a Positive Allosteric Modulator of the Human $Ca^{2+}$receptor, Activates an Extracellular Ligand-bindnig Domain-deleted Rhodopsin-like Seven-transmembrane Structure in the Absence of $Ca^{+}$", JBC Papers in Press, Aug. 31, 2005, pp. 1-15.

Kausik Ray et al., "Evidence of Distinct Cation and Calcimimetic Compound (NPS 568) Recognition Domains in the Transmembrane Regions of the Human $Ca^{2+}$Receptor", The Journal of Biological Chemistry, 2002, pp. 18908-18913, vol. 277, No. 21.

Stephen Rees et al., "GPCR Drug Discovery Through the Exploitation of Allosteric Drug Binding Sites", Receptors and Channels, 2002, pp. 261-268, vol. 8.

Herve Schaffhauser et al., "Pharmacological Characterization and Identification of Amino Acids Involved in the Positive Modulation of Metabotropic Glutamate Receptor Subtype 2", Molecular Pharmacology, 2003, pp. 798-810, vol. 64, No. 4.

Darryle D. Schoepp et al., "Pharmacological agents acting at subtypes of metabotropic glutamate receptors", Neuropharmacology 38, 1999, pp. 1443-1476.

Stephan Urwyler et al., "Positive Allosteric Modulation of Native and Recombinant $\gamma$-Aminobutyric $Acid_B$ Receptors by 2,6-Di-tert-butyl-4-(3-hydroxy-2,2-dimethyl-propyl)-phenol (CGP7930) and its Aldehyde Analog CGP13501", Molecular Pharmacology, pp. 963-971, vol. 60, No. 5 (2001).

* cited by examiner

US 7,611,848 B2

METHOD FOR SELECTING ALLOSTERIC REGULATORS OF CLASS III G PROTEIN-COUPLED RECEPTORS

This application is a 371 of PCT/FR 2004/001140, filed May 11, 2004, which claims priority to French Patent Application No. 03/06136 filed May 22, 2003. The entire contents of each of the above-identified applications are hereby incorporated by reference.

BACKGROUND OF THE INVENTION

The present invention relates to the field of class III G protein-coupled receptors (GPCRs-III), which are involved in many biological phenomena, most of which are essential, in living organisms.

BRIEF SUMMARY OF THE INVENTION

More specifically, the invention falls within the context of the development of effective means for identifying and selecting allosteric regulators of GPCRs-III.

To this effect, the present invention relates to a method for identifying and selecting a compound that acts as an allosteric regulator of a GPCR-III. According to this method, the level of activity of a recombinant GPCR-III (GPCR-III-Z~), essentially depleted of the extracellular domain of the corresponding native GPCR-III, in the presence of a given compound, is compared to that of the same GPCR-III-n in the absence of the compound in question.

This method thus makes it possible to identify and select GPCR-III activators or inhibitors.

The invention is also directed toward the application of such a method to the identification and selection of compounds of interest in fields of activity as varied as pharmacy, the agrofoods industry, the environment, ecology and basic research.

BRIEF DESCRIPTION OF DRAWINGS

The following figures are provided purely by way of illustration and in no way limit the subject of the present invention.

DETAILED DESCRIPTION OF THE INVENTION

Figure 1:
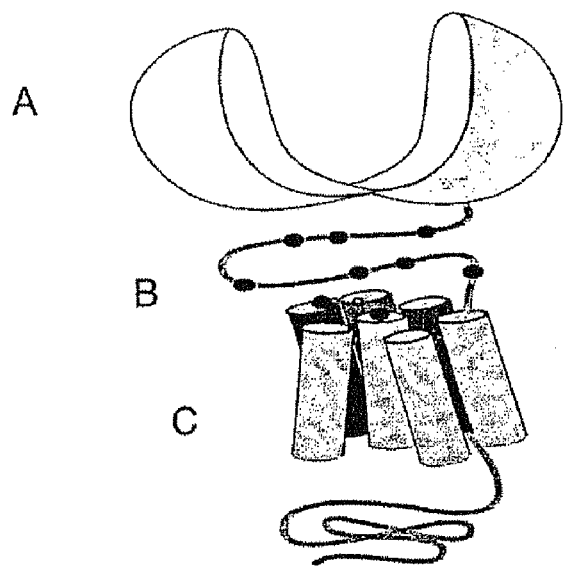
FIG. 1: Diagram of the general structure of a GPCR-III.
  A: outer "Venus flytrap" domain, binding site for orthosteric ligands (or agonists);
  B: cysteine-rich region; and
  C: heptahelical membrane domain, binding site for allosteric regulators.

Comparison of the sequences of the heptahelical domains of GPCRs has made it possible to divide the latter up into three major classes (Bockaert and Pin, 1999).

Class I comprises rhodopsin-like receptors, such as catecholamine receptors, and glycoprotein and peptide hormone receptors.

Class II groups together not only receptors for large peptides such as glucagon and secretin, but also other receptors such as Frizzled, involved in development.

GPCR class III, for its part, comprises receptors activated by the two main neurotransmitters, namely glutamate and 7-aminobutyric acid (GABA), receptors that are calcium ion sensors, putative pheromone receptors, and also receptors which are responsible for detecting sweet and "umami" tastes (amino acids, in particular glutamate).

The present invention relates more particularly to GPCRs-III.

Eight genes encoding glutamate-activated GPCRs-III (also called glutamate metabotropic receptors or mGlu receptors) have been identified in mammals (Conn and Pin, 1997; Pin et al., 2003). These mGlus can be classified in three groups, on the basis of their pharmacology, their sequence similarity and their transduction.

In group I, the mGlu1 and mGlu5 receptors activate phospholipase C (PLC) and appear to act in synergy with glutamate channel receptors. They often appear to be agents that facilitate glutamatergic communication.

Thus, group I mGlu regulators appear to have memory-promoting properties, that are useful for the treatment of diseases such as Alzheimer's disease or schizophrenia.

The group II receptors, mGlu2 and mGlu3, like the group III receptors, mGlu4, mGlu6, mGlu7 and mGlu8, are negatively coupled to adenylyl cyclase. They also regulate the activity of calcium channels and potassium channels. They are often located presynaptically, hence they inhibit glutamate release.

In fact, agonists or positive allosteric regulators of group II or III mGlus exhibit anxiolytic, anti-epileptic, antipsychotic and antiparkinsonian properties, and can decrease the effects of dependency on drugs such as tobacco and cocaine (Conn and Pin, 1997).

A single gene encoding a receptor activated by calcium ions has been identified (Brown and MacLeod, 2001). This receptor plays a key role in regulating blood calcium levels by controlling the release of parathormone, calcium absorption by the bones, and also calcium excretion in the kidneys. It was also thought to have a role at the central level. Mutations in this gene cause diseases such as familial hypocalcuria, severe neonatal hyperparathyroidism (mutations resulting in a loss of function) (Pollak et al., 1993) or autosomal dominant hypocalcemia (mutations resulting in a gain of function) (Pollak et al., 1994).

Furthermore, the inhibition of these receptors will make it possible to correct certain diseases such as osteoporosis.

To date, only two genes encoding $GABA_B$ receptors, GB1 and GB2, have been identified. However, neither GB1 nor GB2 are capable, when they are taken in isolation, of forming a functional $GABA_B$ receptor. The association of the two proteins is in fact necessary for the formation of a receptor with properties similar to the endogenous receptor (Marshall et al., 1999).

The $GABA_B$ receptor was the first GPCR discovered to function only in heterodimeric form. It has thus been shown that GABA binds only to GB1 (Kniazeff et al., 2002), and that GB2 is necessary for the targeting of GB1 to the surface (Pagano et al., 2001). GB2 is also necessary for the high affinity of the agonists on GB1 (Kaupmann et al., 1998). In addition, GB2 is essential for G protein-coupling (Duthey et al., 2002).

The $GABA_B$ receptor therefore constitutes an excellent model for studying the role of GPCR dimerization in their mechanism of activation.

Furthermore, agents that regulate this receptor would 10 make it possible to develop novel treatments against epilepsy and certain forms of pain.

It has also been shown that the T1R1, T1R2 and T1R3 taste receptors function in heterodimeric form (Nelson et al., 2002). These receptors are responsible for the detection of sweet molecules, among which are sweeteners such as aspartame. The discovery of agents that regulate these receptors is of interest in the field of the agrofoods industry.

In accordance with the usual meaning, "orthosteric" ligands, which bind to the active site of GPCRs-III, are distinguished from "allosteric" regulators capable of binding to GPCRs-III at a site other than the active site. In this case, the active site of GPCRs-III is carried by the extracellular domain. Allosteric regulators bind to the membrane domain of GPCRs-II.

Conventionally an "agonist" is a molecule capable, on its own, of increasing the activity of a receptor.

An "antagonist" is a molecule capable of inhibiting the activating effect of an agonist. Among antagonists, "competitive antagonists", which act on the orthosteric site, are distinguished from "noncompetitive antagonists", which act on an allosteric site.

An "inverse agonist" is a molecule capable of inhibiting the constitutive activity of a receptor, i.e. the activity measurable in the absence of any agonist, when such an activity is effectively measurable. An inverse agonist is also capable of inhibiting the effect of an agonist. It is therefore also an antagonist.

A "positive allosteric regulator" is a molecule capable of facilitating the action of an agonist. Such a regulator acts on a site other than the orthosteric site, to which the natural ligand binds.

The expression "facilitating the action of an agonist" is here intended to mean either increasing the power of said agonist (lower concentrations of agonists will then be sufficient to produce the same effect), or increasing its effectiveness (i.e. increasing the maximum response obtained with a saturating concentration of agonist, i.e. a concentration sufficient to occupy all the receptors).

A "negative allosteric regulator" is a molecule capable of decreasing the effect of an agonist, by acting on a site other than the orthosteric site. Such a regulator is also called a "noncompetitive antagonist". As in the case of antagonists, a negative allosteric regulator may or may not possess an inverse agonist activity.

For the purpose of the invention, the expressions "inhibiting the effect of an agonist" and "decreasing 30 the effect of an agonist" are equivalent.

All the GPCRs-III known to date have the particularity that they consist of two distinct protein domains: an extracellular domain called "Venus flytrap", responsible for the binding of the natural ligands (orthosteric ligands), and a heptahelical membrane domain responsible for G protein-coupling and a target for the allosteric regulators (Pin et al., 2003) (FIG. 1). These two domains are separated by a cysteine-rich region.

A second specific characteristic of GPCRs-III lies in their ability to form constitutive dimers, often connected to one another by at least one disulfide bridge.

The construction of a recombinant calcium receptor, truncated in terms of its extracellular domain, has been described by Ray and Northup (2002). The authors investigated, using compounds known to act as allosteric regulators of the human $Ca^{2+}$ receptor, whether or not the transmembrane domain of this receptor comprised structural determinants responsible for ligand binding and for the subsequent activation of said receptor. The authors thus demonstrated that, like the extracellular domain, the heptahelical transmembrane domain contains one or more calcium ion-binding sites. However, the activation of the recombinant receptor by the calcium ions was only detected in the presence of another ligand.

The positive or negative allosteric regulators of GPCRs-II described so far were identified by high-throughput screening techniques.

"Calcimimetics" have been demonstrated for their ability to regulate calcium receptor activity (Nemeth et al., 1998; Hammerland et al., 1998; Hammerland et al., 1999).

Positive regulators of the $GABA_B$ receptor (Urwyler et al., 2001), of the mGlu1 receptor (Knoflach et al., 2001), but also of the mGlu5, mGlu2 and mGlu4 receptors, were presented during the mGlu2002 congress (Taormina, Sicily, Italy, September 2002).

According to the high-throughput screening techniques used up until now, combinatorial libraries are screened using functional tests carried out by means of cell lines stably expressing a GPCR-III. The compounds present in the combinatorial library are tested for their ability to potentiate the effect of a given concentration of agonist.

However, such an approach comes up against multiple difficulties.

Firstly, it is necessary to obtain cell lines stably expressing these receptors. Now, this is a difficult step, especially in the case of glutamate receptors, since this amino acid is present in all culture media and also in serum. In addition, it is produced by most cell lines. Consequently, in practice, it proves difficult, even impossible, to decrease the concentration of glutamate in the culture medium to a level sufficiently low for the receptors not to be activated by the surrounding glutamate.

To remedy this problem, the group Eli Lilly & Co. has developed a cell line that expresses a transporter with a high affinity for glutamate (RGT cells established on the basis of an AV12 line) (Kingston et al., 1998; Schoepp et al., 1997). The cells thus developed control the extracellular glutamate concentration. They maintain this concentration at values sufficiently low for the receptors expressed not to be permanently activated by the glutamate present in the medium. This facilitates the establishment of lines, stably expressing the receptors. However, such a system has drawbacks. In fact, among the compounds tested, some may be taken up by the glutamate transporter and transported into the cells, which can decrease their concentration and prevent their normal action on the receptors. In addition, the ability of some of the molecules tested to inhibit the glutamate transporter can lead to difficulties in carrying out the screening test. In such a case, the concentration of glutamate increases, which results in an artefactual increase in the activity of the receptor. The compound then appears to be a positive allosteric regulator of the receptor, even if it is not really one. A secondary screen is therefore necessary.

Secondly, allosteric regulators quite often have no effect on the GPCR-III if the latter is not simultaneously activated by low doses of agonist. The development of a reproducible and reliable selection test is then made more arduous by the necessary addition of an agonist. The question of the concentration at which the agonist should be used in fact arises. If this concentration is not sufficient or, conversely, is too high, the effect of the allosteric regulator will probably not be detectable. In addition, the signal to noise ratio of the response of the allosteric regulator is reduced because of the increase in the baseline response due to the presence of the agonist.

The present invention makes it possible specifically to circumvent all the problems mentioned above, through the use of recombinant receptors depleted of their extracellular binding domain.

In fact, the invention demonstrates, for the first time, that the membrane domain of a GPCR-III is sufficient to bind allosteric regulators, with an affinity comparable to that observed using the corresponding wild-type receptor.

Thus, these recombinant receptors are insensitive to glutamate.

Advantageously, in the context of the present invention, the allosteric regulators behave, entirely surprisingly, as true agonists or antagonists of the recombinant receptors.

The latter characteristic confers on the present invention a considerable advantage insofar as it is, in practice, easier to study the agonist effect of a molecule on a truncated receptor, than the positive allosteric regulatory effect of said molecule on the corresponding wild-type receptor.

Thus, advantageously, such recombinant receptors can therefore be stably expressed by the cells.

Furthermore, the additional presence of an agonist proves to be unnecessary. Finally, the method, that is the subject of the invention, using these recombinant receptors, makes it possible to obtain a better signal to noise ratio.

According to a first aspect, a subject of the present invention is a method for identifying and selecting a compound that acts as an allosteric regulator of a GPCR-III.

In the context of the invention, a "compound" is defined as being any type of biological or chemical, natural, recombinant or synthetic molecule. For example, a compound may be a nucleic acid (e.g. an oligonucleotide), a protein, a fatty acid, an antibody, a polysaccharide, a steroid, a purine, a pyrimidine, an organic molecule, a chemical radical, etc. The term "compound" also covers the fragments, derivatives, structural analogs or combinations thereof, provided that they act as allosteric regulators of a GPCR-III.

The ability to act as allosteric regulators of a GPCR-III represents the property of interest of the compounds identified and selected by carrying out the method that is the subject of the present invention.

This method comprises at least the following steps:
a) producing a recombinant GPCR-III (GPCR-III-z~) essentially depleted of the extracellular domain of the corresponding native GPCR-III;
b) bringing said compound into contact with said GPCR-III-O;
c) measuring the level $N_1$ of activity of said GPCR-III-Δ in the presence of said compound;
d) comparing the level $N_1$ measured in step c) with the level No of activity of the GPCR-III-Δ in the absence of said compound; and
e) if $N_1$ is significantly different from No. 10, identifying and selecting said allosteric regulator, this method being such that said allosteric regulator behaves like an agonist or an antagonist (or inverse agonist) of said GPCR-III-Δ.

Advantageously, said GPCR-III-L is completely depleted of the extracellular domain of said native GPCR-III.

The implementation of the abovementioned method makes it possible to identify and select compounds that act as allosteric regulators of a GPCR-III by binding to the latter on its heptahelical domain.

According to a first embodiment of the method that is the subject of the invention, if N1 is significantly greater than No, said compound behaves like an agonist of said GPCR-III-Z~, and is a positive allosteric regulator of the whole receptor.

According to a second embodiment of the method that is the subject of the invention, if N1 is significantly less than No, said compound behaves like an inverse agonist of said GPCR-III-O, and is a negative allosteric regulator of the whole receptor.

In the context of the invention, the measurement of the level of activity of the GPCR-III-A can be carried out by any conventional method known to those skilled in the art that is suitable for measuring the activity of a GPCR-III. Among these methods, mention may be made, by way of example, of measurement of the level of production of inositol phosphates (IPs; see Experimental Section, below; Berridge, 1983; Brandish et al., 2003), measurement of GTPγ binding (Milligan, 2003), measurement of intracellular calcium signals using fluorescent markers such as Fluo3 or Fluo4, and measurement of cAMP production, the latter two methods being conventional and well known to those skilled in the art.

The method in accordance with the invention can be carried out with a GPCR-III-L comprising:
 a heptahelical membrane domain, without targeting signal; or
 a targeting signal and a heptahelical membrane domain.

For the purpose of the present invention, the term "targeting signal" is intended to mean a sequence of amino acids, of variable length, in general approximately from 15 to 35 residues, that allows the correct insertion of a receptor in the plasma membrane. In particular, such a targeting signal may be:
 a signal peptide in accordance with the usual meaning; or
 the first 20 amino acids of the N-terminal of rhodopsin, in particular of bovine origin (Ray and Northup, 2002).

When said targeting signal is a signal peptide, this signal peptide may be that of the corresponding native GPCR-III, or that of a different wild-type GPCR-III, or alternatively any known signal peptide. Preferably, said signal peptide is that of said corresponding native GPCR-III.

Advantageously, step a) of the abovementioned method comprises at least the following substeps:
 a1) PCR amplification of a nucleic acid encoding said membrane domain of said GPCR-III-L;
 a2) cloning of the amplification product into a recombinant expression vector;
 a3) transfection of said recombinant vector into a recombinant host cell; and
 a4) production of said GPCR-III-O by said recombinant host cell.

In particular, when a targeting signal is used, substep a2) consists in cloning, into a recombinant expression vector, the amplification product downstream of a nucleic acid encoding said targeting signal.

When the GPCR-III in question has, in its intracellular portion, a signal responsible for its retention in the endoplasmic reticulum (Pagano et al., 2001), it is advisable, beforehand, to render this signal non-functional by mutation, according to conventional mutagenesis methods known to those skilled in the art, in order to allow targeting of the GPCR-III to the plasma membrane.

It is advantageous to place the expression of the nucleic acid encoding the membrane domain of the GPCR-III-Δ, or the coexpression of the nucleic acids encoding the targeting signal and the membrane domain of the GPCR-III-L, under the control of a strong promoter carried by the recombinant vector.

To this effect, those skilled in the art may use any known strong transcriptional promoter. For example, such a strong promoter may be the cytomegalovirus promoter (CMV; see FIG. 2) or that of the SV40 virus.

Many vectors are available to those skilled in the art for constructing the GPCR-III-L1 receptor. Suitable conventional vectors are, in particular, the vectors pRK5-NHA (see Experimental Section below), pcDNA3 (Invitrogen) and pCI (Promega).

In addition, for the purposes of carrying out the method according to the invention, those skilled in the 5 art may use, as recombinant host cell, any type of cell that allows the heterologous expression of a protein. Those skilled in the art may in particular choose from eukaryotic cells, such as yeast cells, HEK293 cells and COS cells, and prokaryotic cells such as bacteria.

In the context of the present invention, the GPCR-III used for carrying out the abovementioned method is chosen from the group comprising:
 glutamate-activated receptors;
 GABA-activated receptors;
 calcium ion-activated receptors;
 putative pheromone receptors; and
 taste receptors.

Preferably, said GPCR-III is chosen from:
 glutamate-activated receptors;
 GABA-activated receptors;
 putative pheromone receptors; and
 taste receptors.

In particular, said GPCR-III is a glutamate-activated receptor, and preferably the mGlu1, mGlu2 or mGlu5 receptor.

Alternatively, said GPCR-III is a GABA-activated receptor, and preferably the GB2 subunit.

According to a second aspect, the present invention relates to the applications of the method as described above, in various fields, in particular in the fields of pharmacy, ecology and the environment, the agrofoods industry, research, etc. directed toward the application of the method defined above for identifying and selecting a compound that is useful in the context of a prophylactic and/or therapeutic treatment in mammals, including humans.

In particular, such a compound may be suitable for implementing a treatment concerning at least one disease among:
 Alzheimer's disease, schizophrenia, nervous disorders, depression, epilepsy, psychosis, drug dependency (glutamate-activated GPCRs-III);
 osteoporosis (calcium-activated GPCRs-III); -epilepsy, pain (GABA-activated GPCRs-III).15

According to a second embodiment, the invention relates to the application of the method described above for identifying and selecting a compound that is useful in the context of a treatment intended to increase or, on the contrary, to reduce the proliferation of living organisms, such as insects and worms, the genome of which contains at least one GPCR-III (Parmentier et al., 1996; Pin et al., 2003).

According to a third embodiment, the invention relates more specifically to taste receptors. In this regard, a subject of the present invention is the application of the method above for identifying and selecting a compound that is useful as a food additive.

In particular, such a food additive is intended to confer a sweet taste, such as a sweetener, or a umami taste, or increases the sensitivity of detection of a sweet compound.

The experimental section hereinafter, supported by 15 examples and figures, illustrates the invention in a nonlimiting manner.

Experimental Section

A. mGlu5 Receptor

1. Construction of the Plasmid Encoding a Truncated GPCR-III Receptor (mGlu5ΔS Protein)

Figure 2:
FIG. 2: Diagram of construction of the plasmid for 10 expression of the truncated receptor mGlu5ΔS.
  PS: signal peptide; VFTM: "Venus flytrap" module; CR: cysteine-rich region; HD: heptahelical membrane domain; CT: intracellular carboxyterminal domain; CMV: cytomegalovirus promoter; HA: hemaglutinin tag.
Figure 2:
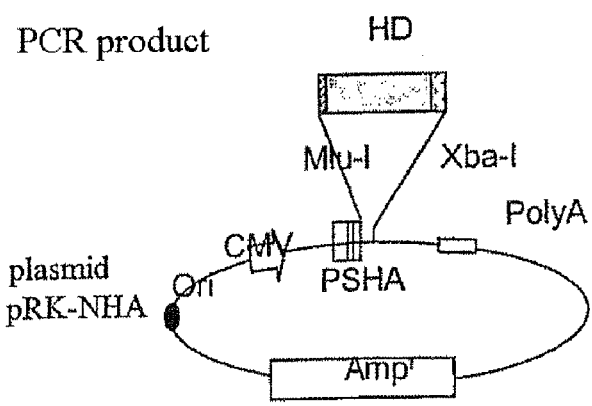
Figure 2:
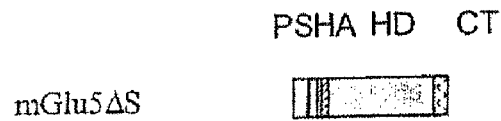

The portion of the cDNA of the mGlu5 receptor encoding its heptahelical domain between residue P568, located 11 residues before the first transmembrane domain, and residue L864, located 37 residues after the 7th transmembrane domain, was amplified by PCR (primers SEQ ID No.1 and SEQ ID No.2), including, respectively, the restriction sites of the Mlu-I and Xba-I enzymes at the 5' and 3' ends (FIG. 2). The PCR product thus obtained was digested with the Mlu-I and Xba-I enzymes, subcloned into the vector pRK5-NHA (FIG. 2), and digested with the same enzymes. The plasmid pRK5-NHA was obtained from the plasmid pRKG5a-NHA (Ango et al., 1999), by replacing the sequence encoding the mGlu5 receptor, from the end of the HA tag to the XbaI restriction site, with an MluI restriction site. The plasmid obtained therefore encodes a protein that has the signal peptide of the mGlu5 receptor, followed by the HA tag (PYD-VPDYA, SEQ ID No.3), and then by the heptahelical domain of the mGlu5 receptor truncated by most of its intracellular C-terminal domain. The expression of this protein is placed under the control of a CMV strong promoter that allows its transient expression after transfection into HEK293 or COS cell lines.

II. Results

II.1. Functional Expression of the Truncated mGlu5ΔS Protein.

After transfection of the plasmid constructed in accordance with the procedure described in part I, into HEK293 cells, the expression of a protein recognized by an anti-HA antibody could be verified by Western blotting and by immunohistochemistry (results now shown). Furthermore, the transfected cells were labeled with the anti-HA antibody even if they were not permeabilized. Because the HA epitope is placed at the N-terminal end of the mGlu5ΔS protein (see FIG. 2), and is therefore located extracellularly, it was proved, by immunohistochemistry, that the protein was correctly targeted to the plasma membrane.

Figure 3:
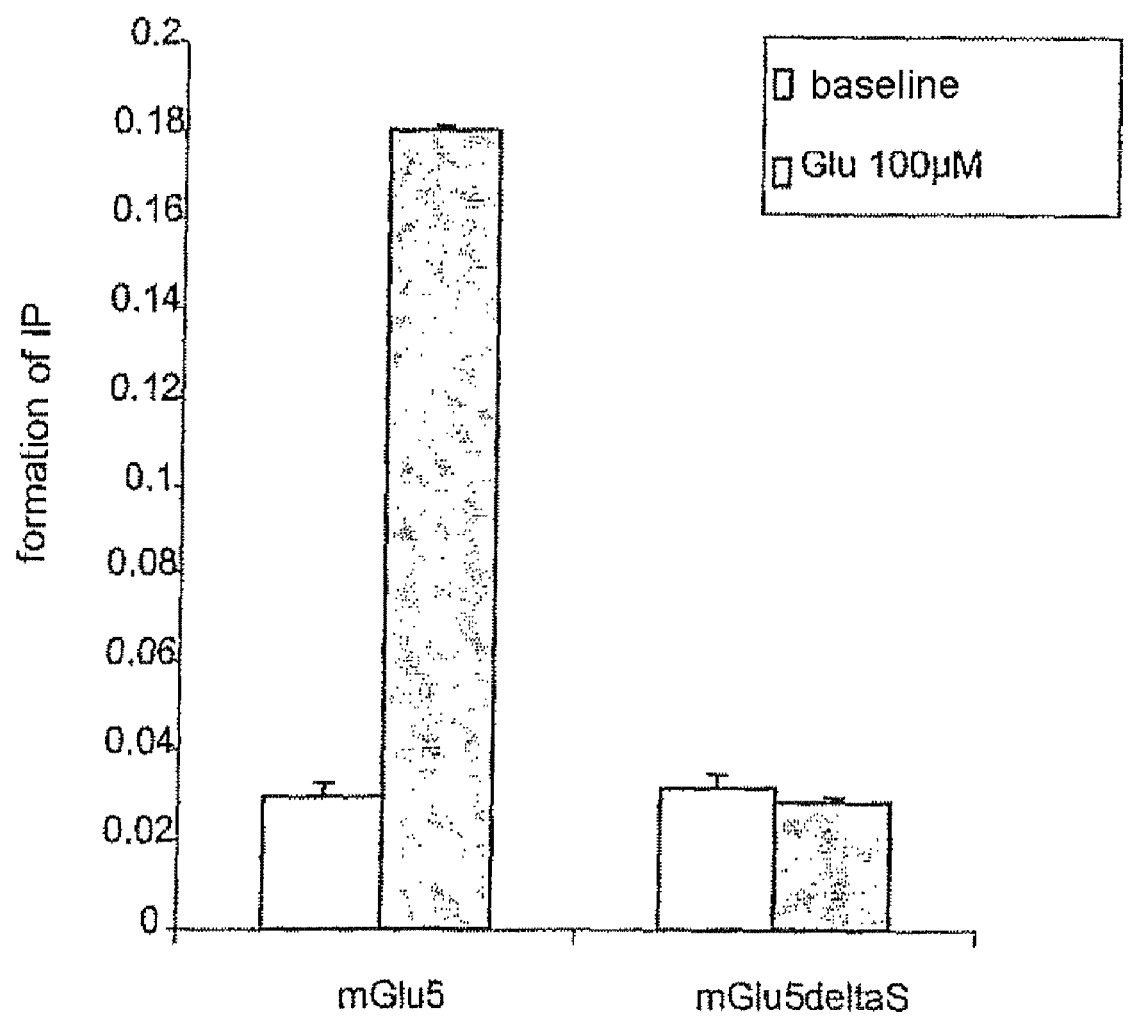
FIG. 3: Graph representing the effect of glutamate on the mGlu5 and mGlu5ΔS receptors in HEK293 cells having been transiently transfected with the cDNA encoding said receptors.
  White columns: baseline IP production;
  Gray columns: IP production in the presence of 100 μM of glutamate.
  The results correspond to the ratio of the production of IP to the radioactivity remaining in the membranes.
  These data correspond to the mean±standard deviation of the mean of triplicates from a representative experiment.

Analysis of the coupling of the wild-type mGlu5 receptor to the inositol phosphate (IP) production pathway in HEK293 cells has shown that this receptor was partially active even in the absence of glutamate (Joly et al., 1995). According to the model of mGlu functioning, it had been proposed that this constitutive activity of the receptor originated from a dynamic equilibrium between inactive states and active states of the heptahelical domain of the receptor (Parmentier et al., 2002). In agreement with this hypothesis, expression of the mGlu5ΔS protein in the HEK293 cells resulted in a greater baseline production of IP than that measured in the control cells. In accordance with the fact that glutamate binds to the outer domain of the receptor, this receptor stimulated IP production in the cells expressing the wild-type mGlu5 receptor, but not in the cells expressing the mGlu5ΔS protein (FIG. 3).

Figure 4:
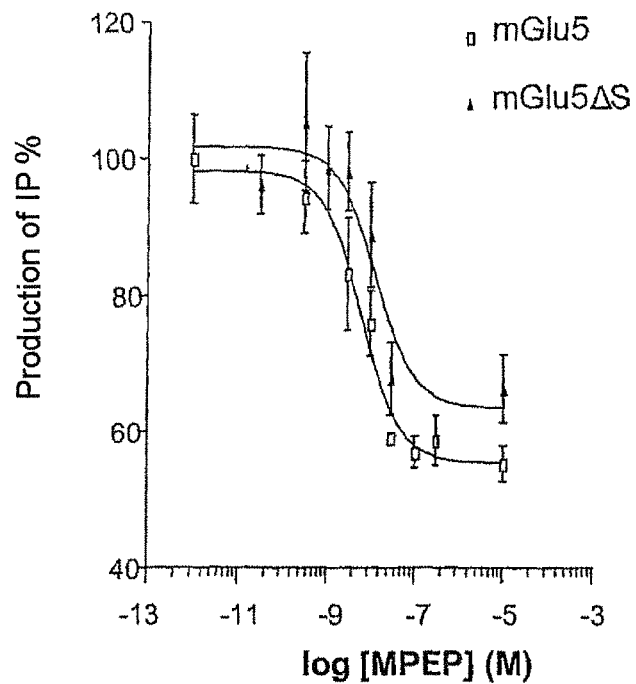
FIG. 4: Graph representing the dose-effect of MPEP on the mGlu5 and mGlu5ΔS receptors in HEK293 cells transiently expressing the mGlu5 (white squares) or mGlu5ΔS (black triangles) receptors. The results correspond to the ratio of the production of IP to the radioactivity remaining in the membranes, and are expressed as percentage baseline production of IP. These data correspond to the mean±standard deviation of the mean of triplicates from a representative experiment.

II.2. Effect of Allosteric Regulators on the Function 10 of the Truncated mGlu5ΔS Protein:

The baseline IP production in the cells expressing the wild-type mGlu5 receptor (control for the constitutive activity of the receptor) could be inhibited with the negative allosteric regulator MPEP (Pagano et al., 2000) with an IC50 (concentration of negative allosteric regulator necessary to obtain 500 of its maximum effect) of 5.7±0.6 μM (n=4) (FIG. 4). This effect of MPEP was also observed on the cells expressing the mGlu5ΔS protein, with an IC50 of 9.8±2.5 μM (n=3) (FIG. 4), which is not significantly different from the value determined on the wild-type receptor. This confirmed that MPEP acts on the heptahelical domain of the receptor, and that the extracellular domain has no influence on its apparent affinity. This result also demonstrated that the baseline activity of IP production in the HEK293 cells expressing the mGlu5ΔS protein indeed results from the ability of this protein to activate the intracellular pathway constitutively.

Figure 5:
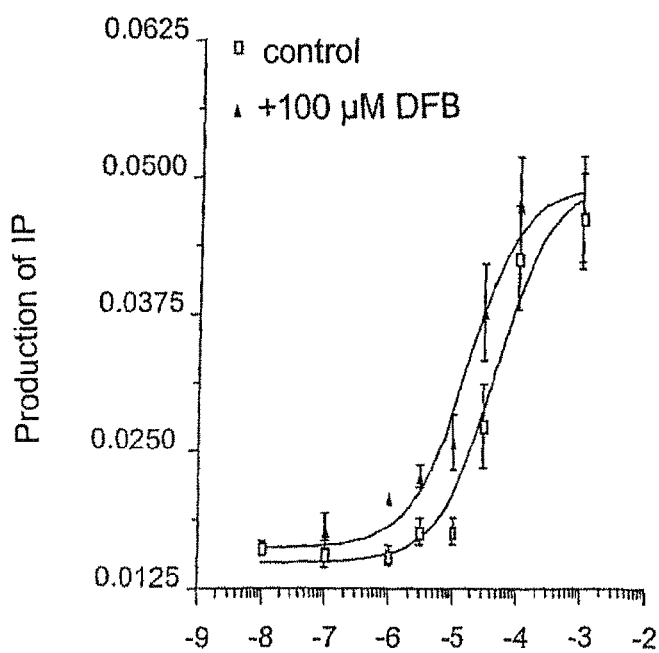
FIG. 5: Graph representing the dose-effect of glutamate on the mGlu5 receptor in the presence (black triangles) or absence (white squares) of DFB, in HEK293 cells transfected with the cDNA encoding said receptor.
  The results correspond to the ratio of the production of IP to the radioactivity remaining in the membranes. These data correspond to the mean±standard deviation of the mean of triplicates from a representative experiment.

DFB has recently been described as a positive allosteric regulator of the mGlu5 receptor (Williams et al., 2002). In order to test its effect on the mGlu5ΔS protein, DFB was synthesized by F. Acher (UMR University R. Descartes, rue des Saints Peres, Paris 5). In accordance with the published data, DFB did not significantly activate the wild-type mGlu5 receptor under conditions where the concentration of glutamate in the incubation medium was kept as low as possible by the coexpression of the glutamate transporter EAAC1, and by the addition of the GPT enzyme (which degrades glutamate in the presence of pyruvate (2 mM)) to the incubation medium (FIG. 5). On the other hand, DFB potentiated the effect of the glutamate and quisqualate agonists, lowering the value of their EC50 (concentration of agonist necessary to obtain 500 of its maximum effect) by a factor of greater than 2 (Table 1 and FIG. 5). In the presence of a low concentration of agonist, DFB increased IP production in a dose-dependent manner, with an EC50 of 1.81±1.04 μM.

Table 1 below shows the potentiation of the effect of glutamate and of quisqualate on mGlu5 by DFB. The EC50 values were determined from dose-effect experiments with glutamate and quisqualate in the presence or absence of DFB, similar to the experiment described in FIG. 5. The data correspond to the mean±standard deviation of the mean of (n) experiments.

TABLE 1

|  | Glutamate | Quisqualate |
| --- | --- | --- |
| Baseline | 47.6 ± 10.1 μM (5) | 20.3 ± 1.0 μM (1) |
| 100 μM DFB | 25.8 ± 5.7 μM (4) | 5.6 ± 1.3 μM (1) |

Figure 6:
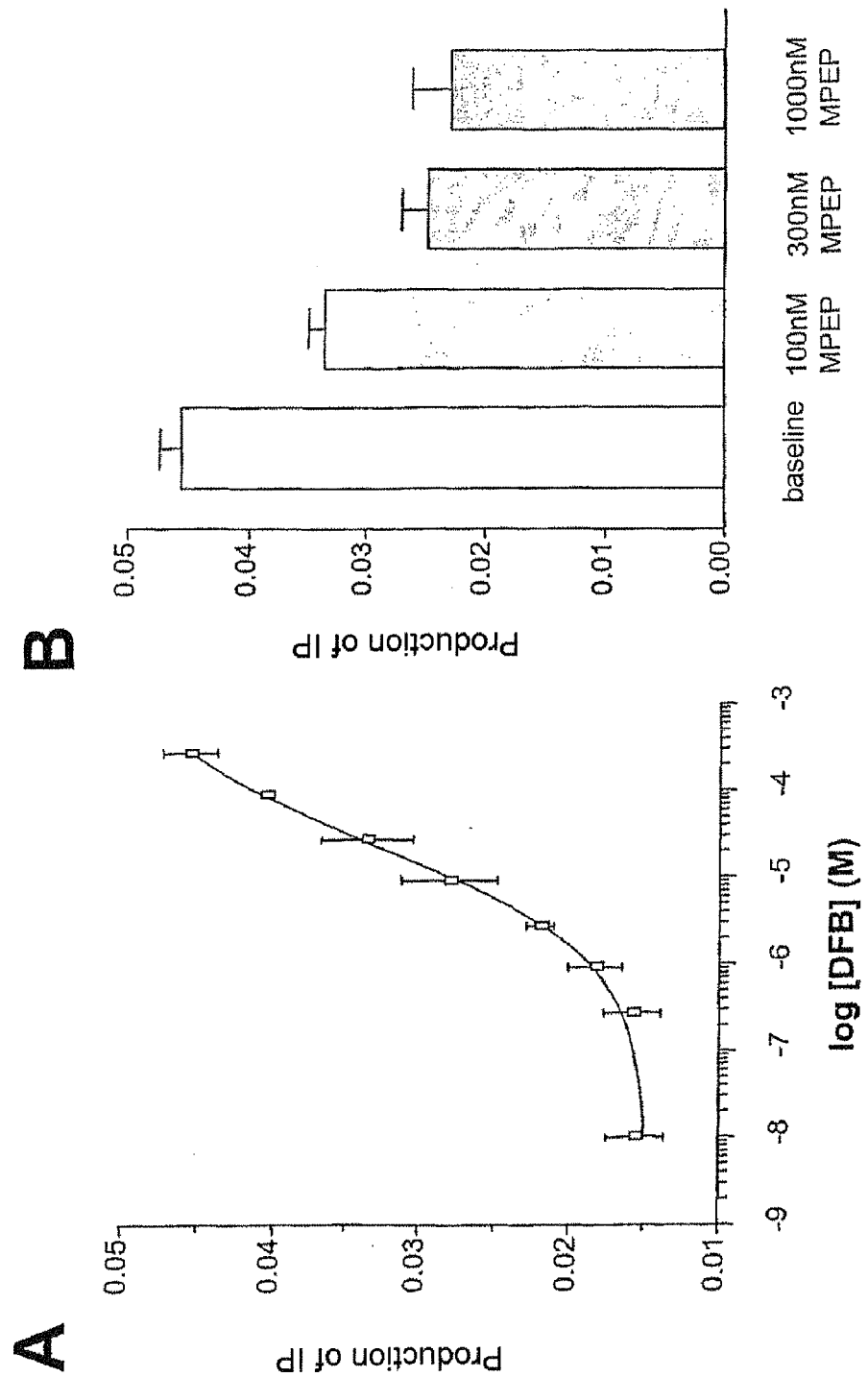
FIG. 6: Graphs representing the dose-effect of DFB on mGlu5ΔS and its inhibition with MPEP.
  A: effect of increasing doses of DFB on the production of IP by HEK293 cells transiently expressing the 15 mGlu5ΔS receptor.
  B: effect of various concentrations of MPEP on the production of IP by cells expressing the mGlu5ΔS receptor, treated with 300 μM of DFB.
  The results correspond to the ratio of the production of IP to the radioactivity remaining in the membranes. These data correspond to the mean±standard deviation of the mean of triplicates from a representative experiment.

On the cells expressing the mGlu5ΔS protein, DFB stimulated IP production, and therefore behaved like an agonist (FIG. 6A). This effect of DFB depended on the concentration of DFB used, with an EC50 of 8.0±3.0 μM (n=3), which is not very different from the EC50 measured for the potentiation of the effect of glutamate on the wild-type receptor, confirming that DFB acts on the heptahelical domain of the receptor. Furthermore, the effect of DFB was inhibited with MPEP, both on the wild-type receptor (data not shown) and on the mGlu5ΔS protein (FIG. 6B), which confirms that the effect of DFB resulted from its action on the mGlu5ΔS protein.

Consequently, the heptahelical domain of the mGlu5 receptor (mGlu5ΔS) is alone capable of activating G proteins, insofar as this portion of the mGlu5 receptor is alone capable of achieving an active conformational state. Furthermore, the negative allosteric regulator (noncompetitive antagonist that has inverse agonist activity) MPEP inhibits the baseline activity of this mGlu5ΔS protein, and DFB is capable of activating this protein. Thus, these molecules do not need the outer domain in order to act.

B. Other receptors

The protocol described in section A.I. above, concerning the mGlu5 receptor, was applied mutatis mutandis to the mGlu1 and mGlu2 receptors and to the GB2 subunit.

In order to demonstrate that the subject of the present invention for the search for positive allosteric modulators applies to all GPCRs-III, truncated receptors were generated according to the same approach as that described for the delta5s construct (mGlu5ΔS).

For this, GPCRs-III for which positive allosteric modulators have been described were chosen: the mGlu1 receptor (Ro01-6128) (Knoflach et al., 2001), the mGlu2 receptor (LY487379) (Schaffhauser et al., 2003), and the $GABA_B2$ (GB2) subunit of the $GABA_B$ receptor (CGP7930) (Urwyler et al., 2001). The receptors truncated with respect to their extracellular and intracellular portions are named, respectively, delta1s, delta2s and deltaGB2s and were expressed transiently in HEK293 cells.

In order to allow the delta2s and deltaGB2s receptors to activate the phospholipase C, and therefore to increase the production of inositol phosphates, these two receptors were coexpressed with the chimeric G protein Gqi9 as described above (Gomeza et al., 1996; Franek et al., 1999).

The compounds Ro01-6128 and CGP7930 were synthesized by F. Acher (University Rene Descarte, Laboratory of Pharmacological and Toxicological Chemistry and Biochemistry, CNRS UMR-8601, 45 rue des Saints Peres, F-75270 Paris Cedex 06), and the compound LY487379 was provided by the company Addex Pharmaceuticals SA (12, Chemin Des Aulx, CH-1228, Plan Les Quates, Geneva, Switzerland).

As described in the literature, the compounds Ro01-6128 [Knoflach et al., 2001] and LY487379 [Schaffhauser et al., 2003] have no agonist effect when they are applied alone to the mGlu1 and mGlu2 receptors, but potentiate the effect of agonists.

Figure 7:
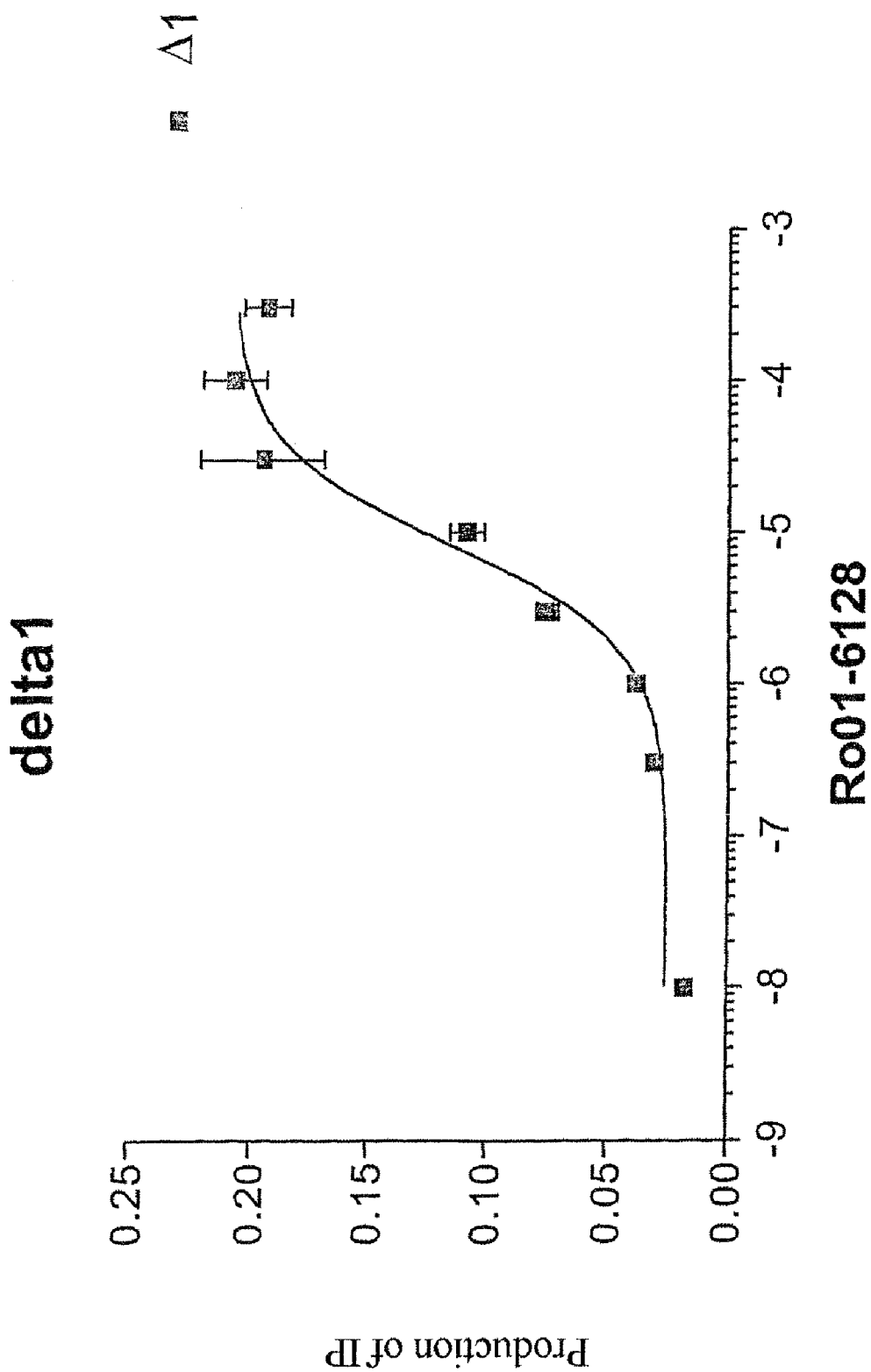
FIG. 7: Graph representing the dose-effect of Ro01-6128 on the delta1s receptor, in HEK293 cells transiently expressing this receptor. The results correspond to the ratio of the production of IP to the radioactivity remaining in the membranes. These data correspond to the mean±standard deviation of the mean of triplicates from a representative experiment.
Figure 8:
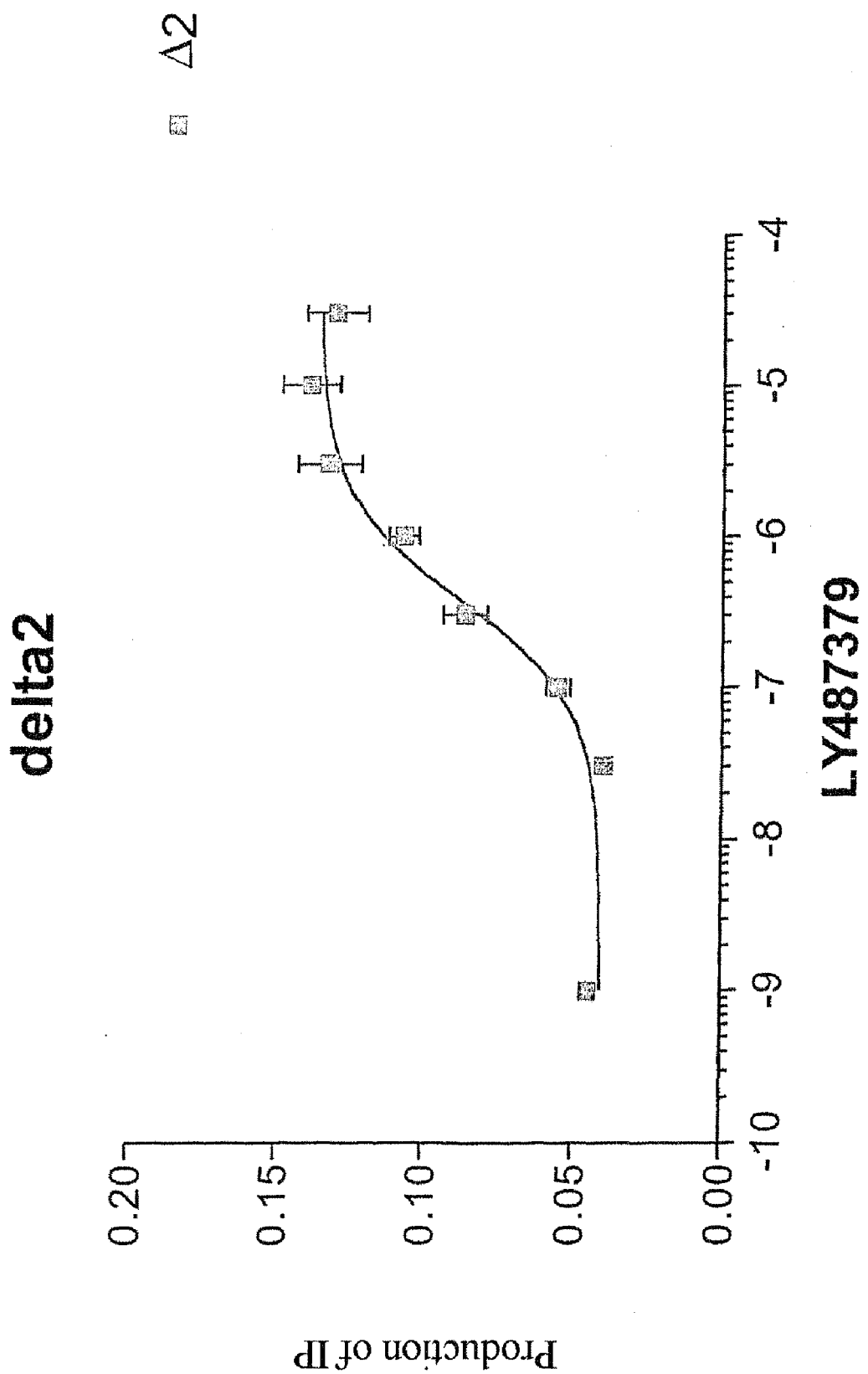
FIG. 8: Graph representing the dose-effect of LY487379 on the delta2s receptor, in HEK293 cells 35 transiently expressing this receptor, and also the chimeric G protein Gqi9 that allows coupling of this receptor to the phospholipase C activation pathway. The results correspond to the ratio of the production of IP to the radioactivity remaining in the membranes. These data correspond to the mean±standard deviation of the mean of triplicates from a representative experiment.

On the other hand, as illustrated in FIGS. 7 and 8, these two compounds activate alone the truncated forms delta1s and delta2s.

Figure 9:
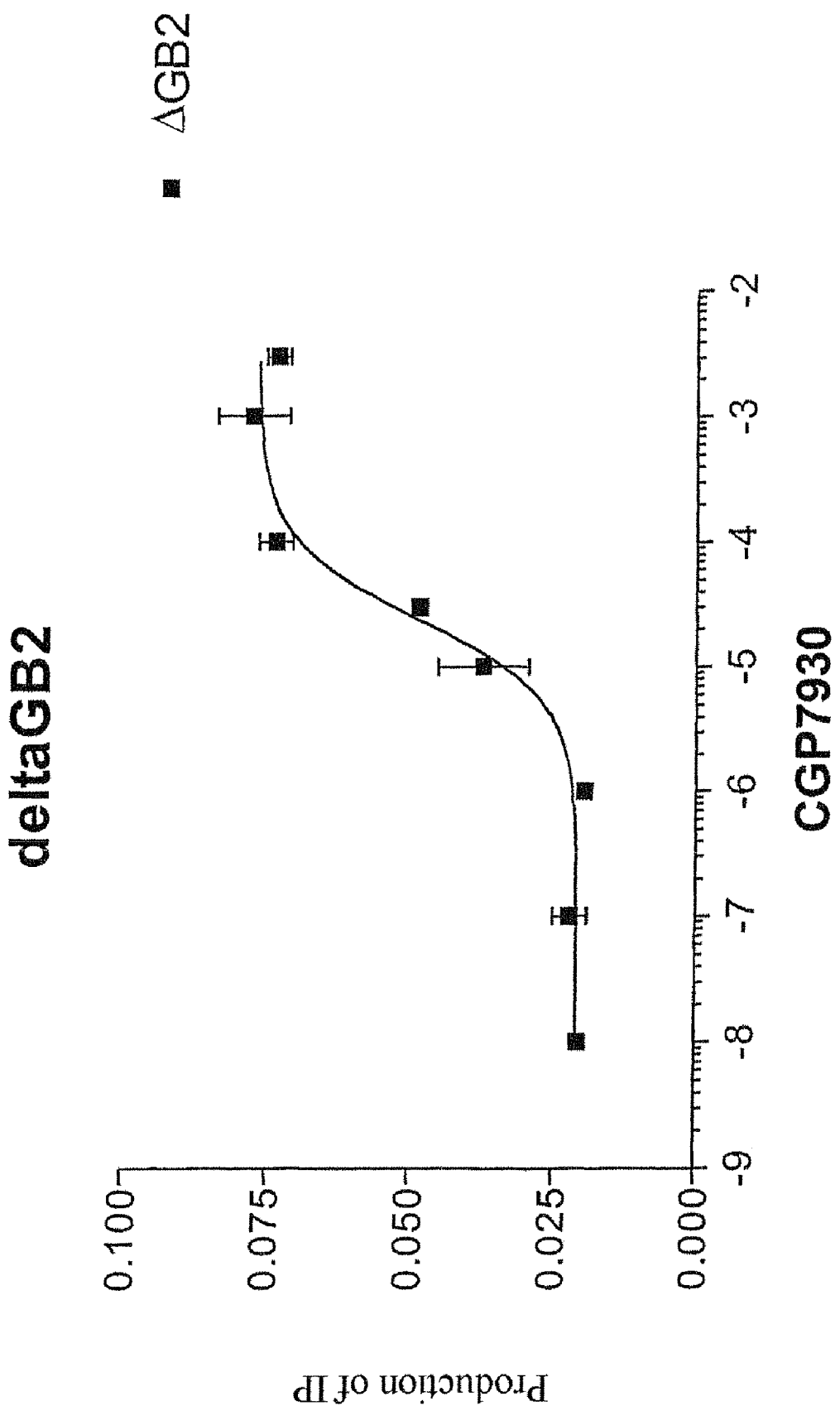
FIG. 9: Graph representing the dose-effect of CGP7930 on the deltaGB2s receptor, in HEK293 cells transiently expressing this receptor, and also the chimeric G protein Gqi9 that allows coupling of this receptor to the phospholipase C activation pathway. The results correspond to the ratio of the production of IP to the radioactivity remaining in the membranes. These data correspond to the mean±standard deviation of the mean of triplicates from a representative experiment.

Similarly, CGP7930, which has only weak agonist activity on the heterodimeric receptor $GABA_B$ (composed of the $GABA_B1$ or GB1, and $GABA_B2$ or GB2 subunits) (Urwyler et al., 2001), strongly stimulates the truncated construct deltaGB2s (FIG. 9).

In fact, the results described in this experimental section demonstrate that proteins corresponding to the heptahelical domain of GPCR-III receptors constitute simple and effective tools for identifying allosteric regulators of these receptors.

REFERENCES

Bockaert J and Pin J-P (1999) Molecular tinkering of G-protein coupled receptors: an evolutionary success. EMBO J 18:1723-1729.
Brown E M and MacLeod R J (2001) Extracellular calcium sensing and extracellular calcium signaling. Physiol Rev 81:239-297.
Conn P and Pin J-P (1997) Pharmacology and functions of metabotropic glutamate receptors. Ann Rev Pharmacol Toxicol 37:205-237.
Duthey B, Caudron S, Perroy J, Bettler B, Fagni L, Pin J-P and Prézeau L (2002) A single subunit (GB2) is required for G-protein activation by the heterodimeric GABAB receptor. J Biol Chem 277:3236-3241.
Joly C, Gomeza J, Brabet 1, Curry K, Bockaert J and Pin J-P (1995) Molecular, functional and pharmacological characterization of the metabotropic glutamate receptor type 5 splice variants: comparison with mGlu1. J Neurosci 15:3970-3981.
Kaupmann K, Malitschek B, Schuler V, Held J, Froestl W, Beck P, Mosbacher J, Bischoff S, Kulik A, Shigemoto R, Karschin A and Bettler B (1998) GABA B-receptor subtypes assemble into functional heteromeric complexes. Nature 396:683-687.
Kniazeff J, Galvez T, Labesse G and Pin J-P (2002) No ligand binding in the GB2 subunit of the GABAB receptor is required for activation and allosteric interaction between the subunits. J Neurosci 22:7352-7361.
Marshall F H, Jones K A, Kaupmann K and Bettler B (1999) GABAB receptors—the first 7™ heterodimers. Trends Pharmacol Sci 20:396-9.
Nelson G, Chandrashekar J, Hoon M A, Feng L, Zhao G, Ryba N J and Zuker C S (2002) An amino-acid taste receptor. Nature 416:199-202.
Pagano A, Rovelli G, Mosbacher J, Lohmann T, Duthey B, Stauffer D, Ristig D, Schuler V, Meigel 1, Lampert C, Stein T, Prézeau L, Blahos J, Pin J-P, Froestl W, Kuhn R, Held J, Kaupmann K and Bettler B (2001) C-terminal interaction is essential for surface trafficking but not for heteromeric assembly of GABAB receptors. J Neurosci 21:1189-1202.
Pagano A, Rüegg D, Litschig S, Stoehr N, Stierlin C, Heinrich M, Floersheim P, Prézeau L, Carroll F, Pin J-P, Cambria A, Vranesic 1, Flor P J, Gasparini F and Kuhn R (2000) The non-competitive antagonists 2-Methyl-6-(phenylethynyl)pyridine and 7-hydroxyiminocyclopropan[b]chromen-1a-carboxylic acid ethyl ester interact with overlapping binding pockets in the transmembrane region of group I metabotropic glutamate receptors. J Biol Chem 275:3375033758.
Parmentier M-L, Prézeau L, Bockaert J and Pin J-P (2002) A model for the functioning of family 3 GPCRs. Trends Pharmacol Sci 23:268-274.
Pin J-P, Galvez T and Prézeau L (2003) Evolution, structure and activation mechanism of family 3/C G-protein coupled receptors. Pharmacol Ther in press.
Pollak M R, Brown E M, Chou Y-H W, Hebert S C, Marx S J, Steinmann B, Levi T, Seidman C E and Seidman J G (1993) Mutations in the human $Ca^{2+}$-sensing receptor gene cause familial hypocaiciuric hypercalcemia and neonatal severe hyperparathyroidism. Cell 75:1297-1303.
Pollak M R, Brown E M, Estep H L, McLaine P N, Kifor 4, Park J, Hebert S C, Seidman C E and Seidman J G (1994) Autosomal dominant hypocalcaemia caused by a $Ca^{2+}$-sensing receptor gene mutation. Nature Genetics 8:303-307.
Williams D L, O'Brien J A, Lemaire W, Chen T-B, Chang R S L, Jacobson M A, Sur C, Pettibone D J and Conn P J (2002) DFB, an allosteric potentiator of mGlu5. Neuropharmacology 43:abs.
Ray and Northup (2002) Evidence for distinct cation and calcimimetic compound (NPS568) recognition domains in the transmembrane regions of the human Ca2+ receptor. J. Biol. Chem. 277: 18908-18913.
Hammerland L, Garrett J, Hung B, Levinthal C, Nemeth E (1998) Allosteric activation of the Ca2+ receptor expressed in *Xenopus laevis* oocytes by NPS 467 or NPS 568. Mol Pharmacol 53:1083-1088.
Hammerland L G, Krapcho K J, Garrett J E, Alasti N, Hung B C, Simin R T, Levinthal C, Nemeth E F, Fuller F H (1999) Domains determining ligand specificity for $Ca^{2+}$ receptors. Mol Pharmacol 55:642-648.
Nemeth E, Steffey M, Hammerland L, Hung B, Van Wagenen B, DelMar E, Balandrin M (1998) Calcimimetics with potent and selective activity on the parathyroid calcium receptor. Proc Natl Acad Sci (USA) 95:4040-4045.
Urwyler S, Mosbacher J, Lingenhoehl K, Heid J, Hofstetter K, Froestl W, Bettler B, Kaupmann K (2001) Positive allosteric modulation of native and recombinant GABAB receptors by 2,6-Di-tert.-butyl-4-4-(3-hydroxy-2,2-dimethyl-propyl)-phenol (CGP7930) and its aldehyde analogue CGP13501. Mol Pharmacol 60:963-971.
Knoflach F, Mutel V, Jolidon S, Kew J N, Malherbe P, Vieira E, Wichmann J, Kemp JA (2001) Positive allosteric modulators of metabotropic glutamate 1 receptor: Characterization, mechanism of action, and binding site. Proc Natl Acad Sci USA 98:13402-13407.
Kingston A E, Ornstein P L, Wright R A, Johnson B G, Mayne N G, Burnett J P, Belagaje R, Wu S, Schoepp D D (1998)

LY341495 is a nanomolar potent and selective antagonist of group II metabotropic glutamate receptors. Neuropharmacology 37:1-12.

Schoepp D D, Johnson B G, Wright R A, Salhoff C R, Mayne N G, Wu S, Cockerham S L, Burnett J P, Belegaje R, Bleakman D, Monn J A (1997) LY354740 is a potent and highly selective group 11 metabotropic glutamate receptor agonist in cells expressing human glutamate receptors. Neuropharmacology 36:1-11.

Berridge M (1983) Rapid accumulation of inositol trisphosphate reveals that agonists hydrolyse polyphosphoinositides instead of phosphatidylinositol. Biochem J 212:849-858.

Brandish P E, Hill L A, Zheng W, Scolnick E M (2003) Scintillation proximity assay of inositol phosphates in cell extracts: High-throughput measurement of G-protein-coupled receptor activation. Anal Biochem 313:311-318.

Milligan G (2003) Principles: Extending the utility of [35S] GTPgS binding assays. Trends Pharmacol Sci 24:87-90.

Ango F, Albani-Torregrossa S, Joly C, Robbe D, Michel J-M, Pin J-P, Bockaert J, Fagni L (1999) A simple method to transfer plasmid DNA into neuronal primary cultures: functional expression of mGluR5 in cerebellar granule cells. Neuro pharmacology 38:793-803.

Parmentier M-L, Pin J-P, Bockaert J, Grau Y (1996) Cloning and functional expression of a *drosophila* metabotropic glutamate receptor expressed in the embryonic central nervous system. J Neurosci 16:6687-6694.

Franek M, Pagano A, Kaupmann K, Bettler B, Pin J-P, Blahos 11 J (1999) The heteromeric GAGA-B receptor recognizes G-protein a subunit C-termini. Neuropharmacology 38: 1657-1666.

Gomeza J, Mary S, Brabet 1, Parmentier M-L, Restituito S, Bockaert J, Pin J-P (1996) Coupling of mGluR2 and mGluR4 to Gα15, Gα16 and chimeric Gαq/i proteins: characterization of new antagonists. Mol Pharmacol 50: 923-930.

Schaffhauser H J, Rowe B A, Morales S, Chavez-Noriega L E, Yin R, Jachec C, Rao S P, Bain G, Pinkerton A B, Vernier J-M, Bristow L J, Varney M A, Daggett L p (2003) Pharmacological characterization and identification of amino acids involved in the positive modulation of metabotropic glutamate receptor subtype 2. Mol Pharmacol 64: 798-810.

The invention claimed is:

1. A method for identifying and selecting a compound that acts as a positive allosteric regulator of a class III G protein-coupled receptor (GPCR-III) selected from the group consisting of:
   glutamate-activated receptors;
   GABA-activated receptors;
   putative pheromone receptors; and
   taste receptors, said method comprising at least the following steps:
   a) producing a recombinant GPCR-III (GPCR-III-Δ) essentially depleted of the extracellular domain of the corresponding native GPCR-III;
   b) bringing said compound into contact with said GPCR-III-Δ in the absence of an agonist of said GPRC-III;
   c) measuring the level $N_1$ of activity of said GPCR-III-Δ in the presence of said compound;
   d) comparing the level $N_1$ measured in step c) with the level $N_0$ of activity of the GPCR-III-Δ in the absence of said compound; and
   e) if $N_1$ is significantly different from $N_0$, identifying and selecting said positive allosteric regulator,
   where said positive allosteric regulator has no effect on the GPCR-III, if GPCR-III is not simultaneously activated by an agonist of GPCR-III, but behaves like an agonist or an inverse agonist of said GPCR-III-Δ.

2. The method of claim 1, wherein said GPCR-III-Δ is completely depleted of the extracellular domain of said native GPCR-III.

3. The method of claim 1, wherein said GPCR-III-Δ comprises a heptahelical membrane domain.

4. The method of claim 3, wherein step a) comprises at least the following substeps:
   a1) PCR amplification of a nucleic acid encoding said membrane domain of said GPCR-III-Δ;
   a2) cloning of the amplification product into a recombinant expression vector;
   a3) transfection of said recombinant vector into a recombinant host cell; and
   a4) production of said GPCR-III-Δ by said recombinant host cell.

5. The method of claim 1, wherein said GPCR-III-Δ comprises a targeting signal and a heptahelical membrane domain.

6. The method of claim 5, wherein said targeting signal is a signal peptide.

7. The method of claim 6, wherein said signal peptide is that of said corresponding native GPCR-III.

8. The method of claim 5,
   wherein said step a) comprises at least the following substeps:
   a1) PCR amplification of a nucleic acid encoding said membrane domain of said GPCR-III-Δ;
   a2) cloning, into a recombinant expression vector, of the amplification product downstream of a nucleic acid encoding said targeting signal;
   a3) transfection of said recombinant vector into a recombinant host cell; and
   a4) production of said GPCR-III-A by said recombinant host cell.

9. The method of claim 4, wherein said recombinant host cell is either a eukaryotic or prokaryotic cell.

10. The method of claim 1, wherein said GPCR-III is a glutamate-activated receptor.

11. The method of claim 10, wherein said glutamate-activated receptor is selected from the group consisting of mGlu1, mGlu2 and mGlu5 receptors.

12. The method of claim 1, wherein said GPCR-III is a GABA-activated receptor.

13. The method of claim 12, wherein said GABA-activated receptor is the GB2 subunit.

* * * * *